(12) United States Patent
Tome et al.

(10) Patent No.: US 8,648,039 B2
(45) Date of Patent: Feb. 11, 2014

(54) USE OF ALPHA-LACTALBUMIN FOR REGULATIONS OF GLYCEMIA

(75) Inventors: Daniel Tome, Paris (FR); Jean-François Huneau, Paris (FR); Takashi Mikogami, Fougeres (FR); Benoit Laplaize, Fougeres (FR)

(73) Assignee: Compagnie Laitiere Europeene, Conde-Neuve-Vire (FR)

( * ) Notice: Subject to any disclaimer, the term of this patent is extended or adjusted under 35 U.S.C. 154(b) by 584 days.

(21) Appl. No.: 12/298,417

(22) PCT Filed: Apr. 24, 2007

(86) PCT No.: PCT/FR2007/000689
§ 371 (c)(1),
(2), (4) Date: Aug. 24, 2009

(87) PCT Pub. No.: WO2007/128901
PCT Pub. Date: Nov. 15, 2007

(65) Prior Publication Data
US 2009/0325872 A1    Dec. 31, 2009

(30) Foreign Application Priority Data
Apr. 27, 2006   (FR) ..................... 06 03810

(51) Int. Cl.
*A61K 38/16*    (2006.01)

(52) U.S. Cl.
USPC .......................................... 514/6.8

(58) Field of Classification Search
None
See application file for complete search history.

(56) References Cited

U.S. PATENT DOCUMENTS

| 4,829,087 A | 5/1989 | Ammon |
| 6,156,738 A | 12/2000 | Bell et al. |

FOREIGN PATENT DOCUMENTS

| EP | 0 604 684 | 7/1994 |
| EP | 1 228 707 | 8/2002 |
| FR | 2 875 680 | 3/2006 |
| WO | WO 02/064090 | 8/2002 |

OTHER PUBLICATIONS

Markus et al. Am. J. Clin. Nutr. 81: 1026-1033, 2005.*
International Search Report for PCT/FR2007/000689 filed Apr. 24, 2007.

* cited by examiner

*Primary Examiner* — Christine J Saoud
(74) *Attorney, Agent, or Firm* — Alston & Bird

(57) ABSTRACT

Use of alpha-lactalbumin in a dietary, health-food or pharmaceutical type of composition to promote the cellular absorption of glucose, to improve the regulation of glycemia, to prevent the appearance of insulin resistance and/or type II diabetes.

6 Claims, 4 Drawing Sheets

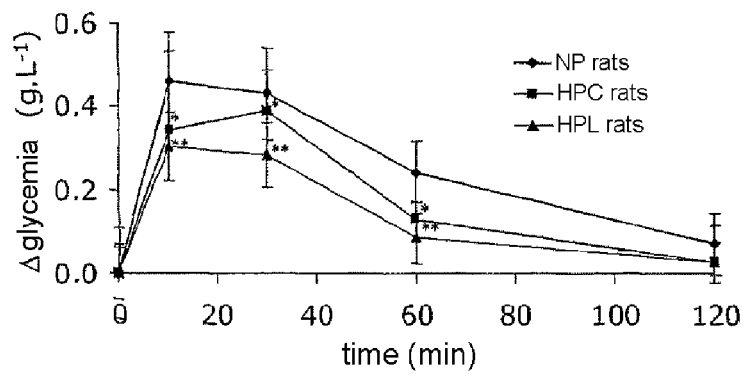
Figure 1: Oral glucose tolerance, comparison of normal protein/high protein diets
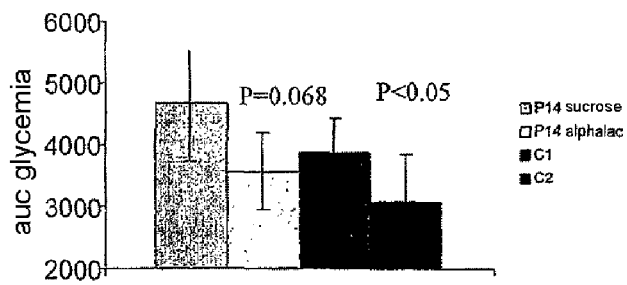
Figure 2: Postprandial glycemia after a first experimental meal
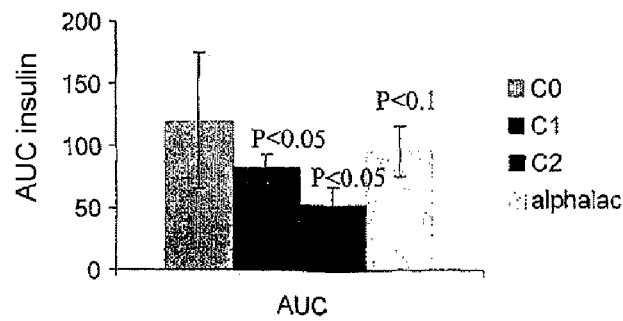
Figure 3: Postprandial insulinemia after a first experimental meal

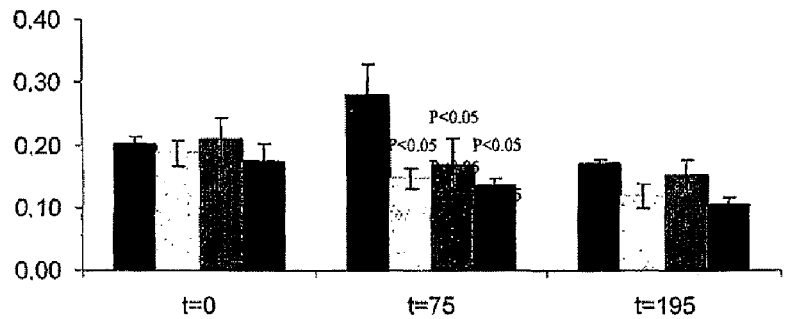
Figure 4: Evaluation of the blood glutathione/total glutathione ratio
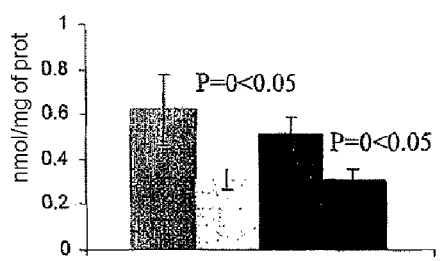
Figure 5: Evaluation of carbonylated proteins in the plasma
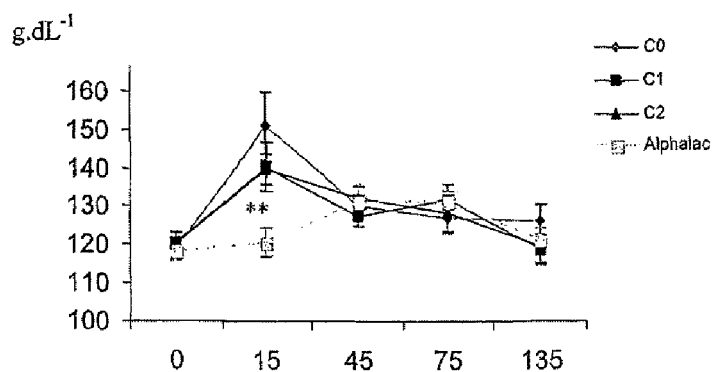
Figure 6: Postprandial glycemia in the glutathione synthesis inhibition phase

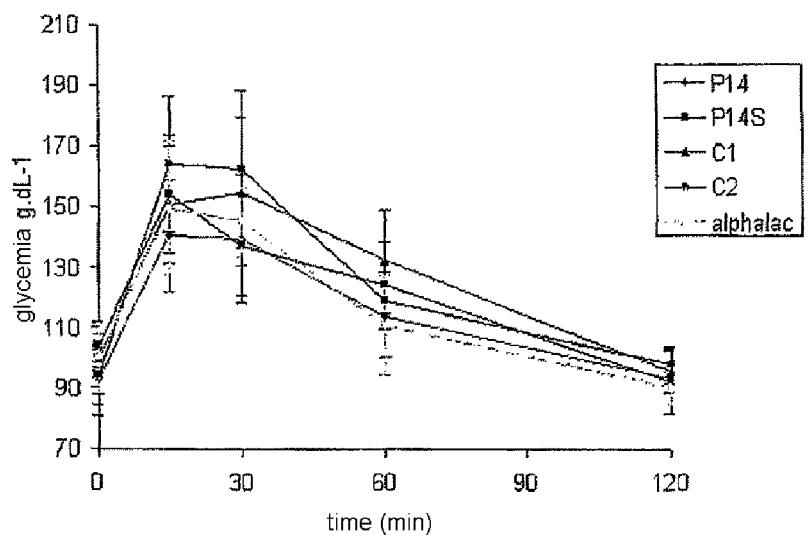
Figure 7: Glucose tolerance test after 5 weeks of sucrose-containing diet
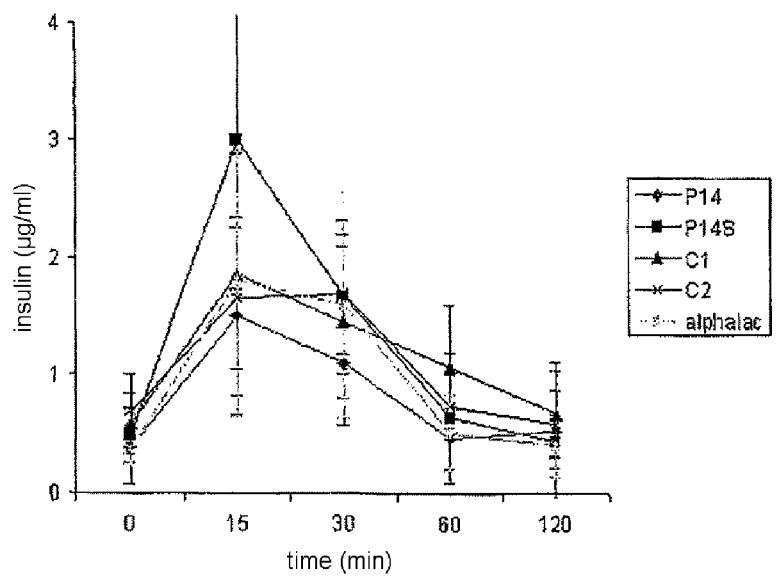
Figure 8: Measurement of insulin after 5 weeks of sucrose-containing diet

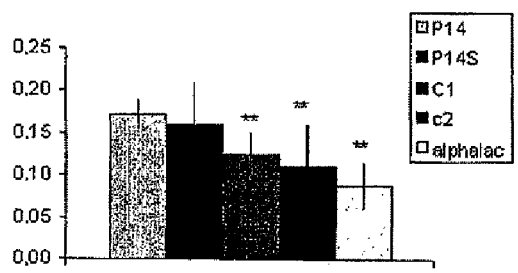
Figure 9: Measurement of fasting blood glutathione after 3 weeks of sucrose-containing diet
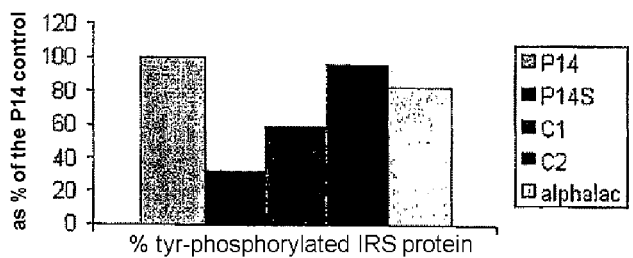
Figure 10: Measurement of phosphorylated IRS proteins after a sucrose-containing diet

USE OF ALPHA-LACTALBUMIN FOR REGULATIONS OF GLYCEMIA

CROSS REFERENCE TO RELATED APPLICATIONS

This application is a national stage application filed under 35 U.S.C. 371 of International Application No. PCT/FR2007/000689, filed Apr. 24, 2007, which claims priority to French Application No. 06 03810, filed Apr. 27, 2006.

FIELD AND BACKGROUND OF THE INVENTION

The invention relates to the use of α-lactalbumin for promoting the cellular absorption of glucose, improving the regulation of glycemia and/or preventing the appearance of insulin resistance and/or type II diabetes. To this effect, the α-lactalbumin can be used in a composition intended to be absorbed enterally or parenterally, whether it is a composition of dietary, dietetic or pharmaceutical type.

Insulin resistance is defined by a reduction in the biological response to the action of insulin and is reflected by a reduced effectiveness of insulin on its target tissues.

Its cause is multifactoral and very complex, and involves the simultaneous intervention of environmental factors and endogenous factors of genetic origin (Pessin J. and Saltiel A. R., 2000, J. Clin. Invest., 106, 165-169).

In the short term, insulin resistance leads to an imbalance in energy metabolism which manifests itself through the phenomenon of postprandial hyperglycemia. In the long term, type II diabetes is the major consequence of insulin resistance.

Type II diabetes is characterized by chronic hyperglycemia without having eaten and abnormally high transient hyperglycemia after the ingestion of a carbohydrate load. This poor regulation of glycemia reflects a weak reaction, by the tissues that perform glucose uptake and metabolism, to the insulin signal (insulin resistance). Hyperglycemia is responsible for the many complications associated with diabetes, at the microvascular or macrovascular level.

In reality, the decreased capacity for regulating glycemia is a gradual phenomenon and a reduced sensitivity to insulin is a prepathological step that marks a considerable risk of developing diabetes. The nature of the diet affects the appearance of a reduced sensitivity to insulin, but the influence of the amount and of the nature of the proteins in the diet has remained relatively unexplored.

The favorable action of fish proteins, in particular of cod proteins, in the regulation of glycemia, the improvement of glucose tolerance and the prevention of the appearance of insulin resistance has been demonstrated in the studies by C. Lavigne et al., Am. J. Physiol. Endocrin. Metab. 281: E62-E71, 2001; F. Tremblay et al., Diabetes. 52: 29-37, 2003; C. Lavigne et al., Am. J. Physiol. Endocrin. Metab. 278: E491-E500, 2000.

Fish proteins are found to be more effective than soybean proteins and casein, although their amino acid compositions are relatively similar. The use of fish proteins in a dietary, dietetic or pharmaceutical composition as an additive for improving the cellular absorption of glucose and/or the regulation of glycemia has, however, several drawbacks:

The fish protein fractionation industry is not currently at a very advanced level of development, in particular by comparison with the soybean or milk industry. The extraction of such proteins from fish meat would cause the latter to lose most of its market value, thereby resulting in prohibitive costs.

An objective of the present invention was to find a product having the properties of regulating glycemia, promoting the cellular absorption of glucose, improving insulin sensitivity, and/or preventing the appearance of type II diabetes. A product which is both easy to prepare and economical and can be readily used as a food additive without harming the gustatory and/or olfactory qualities of the food into which it is incorporated was sought.

A subject of the present invention is the use of α-lactalbumin in a dietary composition or for the preparation of a pharmaceutical composition as a glycemia-regulating agent, for promoting the cellular absorption of glucose and/or for preventing the appearance of type II diabetes. α-lactalbumin is a milk protein. It is the second most predominant protein of milk serum, or lactoserum, in terms of its percentage by weight, after lactoferrin or β-lactoglobulin for human milk or bovine milk, respectively.

Document WO 02/064090 discloses a food supplement containing milk serum proteins enriched in α-lactalbumin, a low-glycemic-index sugar, fats, caffeine and a source of 5-hydroxytryptophan. This food supplement is intended for individuals in a state of stress. It makes it possible to increase the serotonin level in an individual. The low-glycemic-index sugars enable delayed glucose and insulin release. The α-lactalbumin promotes the increase in serotonin by providing tryptophan which is a serotonin precursor.

In addition, document EP-1 228 707 discloses the use of α-lactalbumin or of an α-lactalbumin-enriched milk serum protein concentrate as a prebiotic food or as a food supplement or additive. The use of α-lactalbumin is intended to reinforce the intestinal microbial population by promoting its growth. These food supplements can be used for the treatment of gastroenteritis.

Document U.S. Pat. No. 6,156,738 describes the use of food supplements in the form of bars comprising simple sugars, proteins, lipids and complex sugars. These food supplements make it possible to regulate nocturnal hypoglycemia in insulin-dependent diabetics. Milk serum and lactalbumin are mentioned among the proteins that can be used. The mechanism of function proposed by the authors is the following: the sugars are released in 3 phases over the course of the night: rapid release of the simple sugars, release of sugars from the proteins converted by the liver, release of the slow sugars. In this document, the general term lactalbumin is used to denote lactoserum (total) proteins and not α-lactalbumin.

In addition, the proteins are used in these food supplements as a source of sugars and not as a regulator of the assimilation of glucose originating from another source. Consequently, the use of α-lactalbumin for promoting glucose assimilation and/or regulating glycemia and/or preventing the appearance of type II diabetes and/or preventing insulin resistance is neither mentioned nor suggested by this document.

α-lactalbumin has also been mentioned for its potential role as an anticarcinogenic agent (G. H. McIntosh et al., Int. Dairy Journal, 5: 425-434, 1998), and as a food additive for preventing lipid oxidation and promoting the reduction of adipose tissues (J-C. J. Bouthegourd et al., Am. J. Physiol. Endocrinol. Metab., 283: E565-E572, 2002). It is also known, by virtue of the article "Les propriétés des protéins de petit lait" [The properties of whey proteins] Nutranews Jan. 11, 2003, that caseins and lactoserum proteins inhibit the renin-angiotensin-aldosterone system and, in this respect, would have the capacity to reduce body fat and also the diseases which are associated therewith, such as type II diabetes (G. H. Gossens et al., Obesity Reviews, 4: 43, 2003). However, this document does not mention a particular capacity of α-lactalbumin for preventing or treating insulin resistance and/or type II diabetes.

Finally, glutathione is capable of modulating oxidative stress, and a hypothesis regularly proposed consists in attributing the deleterious effects of poor glycemic control to the oxidizing role of glucose (A. Ceriello et al., Diabetes Care, 25: 1439, 2002). In addition, studies have shown that glutathione can modulate glucose tolerance or insulin sensitivity (G. Paolisso et al., Am. J. Physiol. 263: E435, 1992; M. Khamaisi et al., Biochem. J., 349: 579, 2000). Consequently, since the cysteine content in the diet acutely and chronically influences the glutathione content of the organism (L. C. Lands et al., J. Appl. Physiol. 87: 1381, 1999; M. H. Stipanuk et al., J. Nutr. 132: 3369, 2002), it was possible to put forward the hypothesis that α-lactalbumin, simply by virtue of its cysteine content, was capable of limiting oxidative stress and of promoting insulin sensitivity, and could therefore curb the prepathological progression of glucose intolerance. However, tests disclosed in the experimental section show that the mere cysteine content of α-lactalbumin is not sufficient to explain the action of this protein on the regulation of glycemia and glucose tolerance.

SUMMARY OF THE INVENTION

A subject of the invention is the use of α-lactalbumin or of an α-lactalbumin hydrolysate for improving glucose tolerance and/or promoting the cellular absorption of glucose and/or preventing glucose intolerance and/or promoting the regulation of glycemia and/or preventing or treating the appearance of insulin resistance and/or preventing or treating the appearance of the symptoms of type II diabetes and/or preventing or treating the appearance of type II diabetes.

A subject of the invention is more particularly the use of α-lactalbumin or of an α-lactalbumin hydrolysate for the preparation of a medicament for use in improving glucose tolerance and/or promoting the cellular absorption of glucose and/or preventing glucose intolerance and/or promoting the regulation of glycemia and/or preventing or treating the appearance of insulin resistance and/or preventing or treating the appearance of the symptoms of type II diabetes and/or preventing or treating the appearance of type II diabetes.

A subject of the invention is also the use of α-lactalbumin or of an α-lactalbumin hydrolysate for the preparation of a dietary composition, optionally of a dietetic composition, for use in improving glucose tolerance and/or promoting the cellular absorption of glucose and/or preventing glucose intolerance and/or promoting the regulation of glycemia and/or preventing or treating the appearance of insulin resistance and/or preventing or treating the appearance of the symptoms of type II diabetes and/or preventing or treating the appearance of type II diabetes.

A subject of the invention is also a method for preparing a dietary composition, optionally a dietetic and/or pharmaceutical composition, for use in improving glucose tolerance and/or promoting the cellular absorption of glucose and/or preventing glucose intolerance and/or promoting the regulation of glycemia and/or preventing or treating the appearance of insulin resistance and/or preventing or treating the appearance of the symptoms of type II diabetes and/or preventing or treating the appearance of type II diabetes, characterized in that it comprises at least one step consisting in introducing α-lactalbumin or an α-lactalbumin hydrolysate into a dietary composition, optionally a dietetic composition, or into a pharmaceutically acceptable carrier.

In fact, as is demonstrated below in the experimental section, α-lactalbumin makes it possible to control the hyperglycemia subsequent to the cellular absorption of glucose. It also makes it possible to prevent the appearance of the insulin resistance phenomenon. The consequence of these properties is a beneficial effect on the prevention of type II diabetes and the appearance of the symptoms which are associated therewith.

This property is observed much more markedly for α-lactalbumin than for total milk proteins.

α-lactalbumin is the second most predominant protein, in terms of its percentage by weight, in lactoserum. Bovine α-lactalbumin is a 14.2 kD protein comprising 123 amino acids.

The α-lactalbumin that can be used in the present invention may originate from human milk, cow's milk, goat's milk, ewe's milk, mare's milk, buffalo milk or milk from any other mammal.

Purified bovine α-lactalbumin may be used: this product may be prepared by various methods known to those skilled in the art, such as that described in EP-1 017 286. It is commercially available from the company ARLA FOODS under the trade mark LAC PRODAN ALPHA 20® or from the company DAVISCO under the trade mark BIOPURE-ALPHA-LACTABUMIN®.

It may also be envisioned to use an α-lactalbumin enriched protein mixture, for instance a lactoserum enriched with at least 30% by weight of α-lactalbumin relative to the total weight of the proteins, preferably at least 40%, and even more preferably at least 50% by weight of α-lactalbumin, such as the product VITALMOR α-607® sold by the company ARMOR PROTEINES.

Finally, in accordance with the present invention, an α-lactalbumin hydrolysate may be used. The term "α-lactalbumin hydrolysate" is intended to mean a partial or total hydrolysate of α-lactalbumin. It may therefore be a mixture of peptides and/or of amino acids, derived from the hydrolysis of α-lactalbumin. This hydrolysis may have been carried out chemically or by means of an enzyme digestion.

The proteins and the protein mixtures that can be used in accordance with the present invention are advantageously used under the following conditions:

The invention relates more particularly to the prevention and/or treatment of the pathologies stated above in humans.

Whether it is a dietary supplement, optionally a dietetic supplement, or a pharmaceutical composition, the daily dose of α-lactalbumin is between 2 and 100 grams. This dose is adjusted as a function of the weight and age of the individual and of his or her morphotype, according to whether it is in relation to a predisposition to type II diabetes. For an adult individual of average height and weight, a daily consumption of 10 to 80 g, preferably of 20 to 70 g, even more preferably of 30 to 50 g of α-lactalbumin is envisioned, i.e. between 10% and 80% by weight of the total daily protein consumption for this individual, preferably from 20% to 70%, even more preferably between 30% and 50%.

In accordance with the present invention, the α-lactalbumin is used under the following conditions:

It may be incorporated into a dietary composition, optionally a dietetic composition, in particular into a composition based on milk or on milk-derived products, for example by adding the α-lactalbumin to the milk base of this composition and carrying out the preparation of the food composition according to a customary process. It is, for example, possible to incorporate α-lactalbumin into milk and to use this mixture to prepare yoghurts, cheeses, dessert creams, concentrated milk and any other milk-based food, such as, for example, spreadable cheese specialty product, instant powder to be diluted in milk or water, confectionery, chocolate, ice cream or milk drink.

The dietetic compositions may be in the form of ready meals, such as powders to be diluted in water or milk, sweet or savory creams, or soups. The compositions generally have a high protein content (at least 50% by weight of proteins relative to the total weight of the composition) and a low fat and/or sugar content. They are packaged in the form of meal doses. An appropriate amount of α-lactalbumin may be incorporated therein as a substitution for or a supplement to the other protein constituents, depending on the indication and the type of diet concerned.

The dietetic compositions may also be in the form of gel capsules, tablets, powders or syrups with a high concentration of α-lactalbumin, optionally in combination with a suitable excipient such as gelatin, lactose, etc.

The pharmaceutical compositions may also be in the form of powders, gel capsules, tablets or syrups. Like the dietetic supplements, they may comprise other constituents, such as other proteins, vitamins and pharmaceutically acceptable excipients. According to one variant of the invention, they may also be in a form which allows them to be administered rectally, sublingually, subcutaneously or intradermally. These dietetic or pharmaceutical compositions, which are not directly incorporated into the food but which are to be consumed in the form of unit doses, will preferably be administered at mealtimes, advantageously within a period ranging from one hour before the meal to a quarter of an hour after the meal, preferably between half an hour before the meal and up to the meal itself. Advantageously, these supplements are consumed during the meal itself or during the quarter of an hour preceding the meal.

EXPERIMENTAL SECTION

Brief Description of the Drawings

Figures:

FIG. 1: Oral glucose tolerance, comparison of normal protein/high protein diets.

FIG. 2: Postprandial glycemia after a first experimental meal.

FIG. 3: Postprandial insulinemia after a first experimental meal.

FIG. 4: Evaluation of the blood glutathione/total glutathione ratio.

FIG. 5: Evaluation of carbonylated proteins in the plasma.

FIG. 6: Postprandial glycemia in the glutathione synthesis inhibition phase.

FIG. 7: Glucose tolerance test after 5 weeks of sucrose-containing diet.

FIG. 8: Measurement of insulin after 5 weeks of sucrose-containing diet.

FIG. 9: Measurement of fasting blood glutathione after 3 weeks of sucrose-containing diet.

FIG. 10: Measurement of phosphorylated IRS proteins after a sucrose-containing diet.

EXAMPLE 1

Comparison Between Normal Protein/High Protein Diets

Experiments were carried out in three groups of 8 male rats of the Wistar Hannover strain, which received either a standard diet (normal protein including 14 energy % of total milk proteins, and denoted "NP"), or a standard high protein diet (55 energy % including total milk proteins, and denoted "HPC"), or a test high protein diet (55 energy % including a serum protein concentrate enriched in α-lactalbumin YV9705 prepared by the company ARMOR PROTEINES, and denoted "HPL").

The compositions of the various foods (NP, HPC or HPL) are given in the table below in g/kg of food.

|  | NP | HPC | HPL |
| --- | --- | --- | --- |
| Total milk proteins | 140 | 530 | 0 |
| YV9705 | 0 | 0 | 530 |
| Sucrose | 100.3 | 46.5 | 46.5 |
| Corn starch | 622.4 | 286.2 | 286.2 |
| Vitamin compound AIN 93 VX | 10 | 10 | 10 |
| Mineral compound AIN 93M | 35 | 35 | 35 |
| Soybean oil | 40 | 40 | 40 |
| Cellulose | 50 | 50 | 50 |
| Choline bitartrate | 2.3 | 2.3 | 2.3 |

The protein compositions of various protein fractions are given in the table below.

|  | Total milk proteins | YV9705 |
| --- | --- | --- |
| Casein | 80% | 0% |
| β-lactoglobulin | 11% | 15% |
| α-lactalbumin | 4% | 60% |
| Serum albumin | 1% | 20% |
| Others | 4% | 5% |

After 8 weeks of diets, the rats are sacrificed by euthanasia: blood and various tissue samples are taken (liver, subcutaneous white adipose tissue, visceral white adipose tissue, brown adipose tissue, kidney, adrenals, intestinal mucosa). The mean body compositions of the rats of various groups are given in the table below.

|  | NP group | HPC group | HPL group | Diet effect (p♣) | Diet effec♣ with FC as covariable |
| --- | --- | --- | --- | --- | --- |
| Live weight | 359.86 ± 18.9$^a$ | 346.7 ± 20.8$^{ab}$ | 330 ± 17.38$^b$ | P < 0.05 | NS |
| Liver | 10.58 ± 1.45$^a$ | 9.94 ± 0.76$^a$ | 10.24 ± 0.93$^a$ | NS | NS |
| Epidydimal AT | 8.58 ± 1.38$^a$ | 7.63 ± 1.36$^{ab}$ | 6.21 ± 1$^b$ | P < 0.05 | NS |
| Perirenal AT | 11.03 ± 3.2$^a$ | 8.2 ± 1.17$^b$ | 5.49 ± 0.79$^c$ | P < 0.0001 | NS |
| Subcutaneous | 9.27 ± 2.4$^a$ | 7.88 ± 1.66$^{ab}$ | 6.15 ± 0.67$^b$ | P < 0.05 | NS |

-continued

|  | NP group | HPC group | HPL group | Diet effect (p)♣ | Diet effect♣ with FC as covariable |
|---|---|---|---|---|---|
| AT Total white | 28.89 ± 6.62$^a$ | 23.71 ± 3.41$^a$ | 17.84 ± 1.68$^b$ | P < 0.05 | NS |
| AT Brown | 0.77 ± 0.13$^a$ | 0.66 ± 0.16$^{ab}$ | 0.49 ± 0.13$^b$ | P < 0.05 | NS |
| AT Carcass | 10.58 ± 1.45$^a$ | 9.94 ± 0.76$^a$ | 10.24 ± 0.94$^a$ | NS | NS |

*Means ± standard deviations
AT: adipose tissue;
FC: food consumption.

♣Estimated by a Fisher F test, obtained using a mixed model
The means which do not share the same suffix are significantly different (comparisons obtained by means of contrasts, in the mixed model).

The gain in weight by the rats over eight weeks is smaller in the rats subjected to an HPL diet. This result comes mainly from a 35% decrease in the development of the white adipose tissue in the HPL rats, the weight of the other tissues remaining the same. Since the average energy consumption by the rats is lower on the high protein diet, a part of the body composition results could be explained by lower consumptions on the high protein diet. However, this HPL group has an energy consumption equivalent to that of the HPC group, although the effects of the diet on the body composition are more marked, thereby suggesting that the nature of the protein (serum proteins enriched in α-lactalbumin versus total milk protein) influences the body composition on the high protein diet.

The oral glucose tolerance tests show that, after only 4 weeks of diet, the HPL rats have a much better ability to limit the shifts into hyperglycemic state after ingestion of a glucose load (FIG. 1).

In order to summarily compare the glucose tolerance, we calculated the areas under the glycemia curve for each of the groups, at days 0 and 27. The table below gives these results, and also those of the statistical analyses. While, for all 3 groups, no drift in glucose tolerance is noted between D0 and D27 (age effect not significant), a significant diet×age interaction, with significant reduction of the area under the curve, is observed at D27 in the HPL group, and therefore a better glucose tolerance, relative to the NP group.

These results indicate that it appears to be possible, by adjusting the quality and the quantity of proteins through monitoring the diet, to influence glucose tolerance and the body composition and to limit the appearance of prepathological phenomena associated with type II diabetes.

|  | NP | HPC | HPL | Diet × age interaction (p)* |
|---|---|---|---|---|
| Day 0 | 26.5 ± 10.5$^a$ | 24.1 ± 8.1$^a$ | 32.2 ± 8.4$^a$ | 0.03 |
| Day 27 | 30.5 ± 8.9$^a$ | 22.5 ± 10.5$^{ab}$ | 17.9 ± 8.8$^b$ |  |
| Age effect* |  | P = 0.15 |  |  |

Means ± standard deviations (g · min · L − 1).
*Estimated by means of a Fisher F test, obtained using a mixed model.

The means which do not share the same suffix are significantly different (comparisons obtained using contrasts, in the mixed model).

EXAMPLE 2

Results Obtained on Normal Protein Diets in a Context of Nutritional Induction of Glucose Intolerance Methodology:

Dietary/physiological context: we used a model diet containing 14 energy % of proteins, in which the carbohydrates are provided only in the form of sucrose. This diet induces glucose intolerance gradually in a few weeks in sedentary rats. This diet constitutes a good dietary/environmental model for testing the influence of the nature of the proteins in the diet.

Physiological evaluation: rather than oral glucose tolerance tests, the model makes it possible to monitor the shift into a hyperglycemic state in a postprandial situation (after a calibrated meal). This model is close to a real dietary situation in humans. The reality of shifts into a glycemic state after a meal is a relevant criterion which makes it possible to determine the seriousness of the dietary stimulus or, on the contrary, the preventive capacity of the diet acutely or chronically (Gavin, J. R., 3rd, Int. J. Clin. Pract. Suppl. 107: 14, 1999). These tests are carried out at the instigation of the diet (acute) and after 2 and 4 weeks of diets.

In parallel, these tests also make it possible to determine, in the postprandial phase, the change in insulinemia, and plasma amino acid concentrations, and to monitor the glutathione status in the blood in order to relate the latter to the postprandial glycemic shift. Finally, other parameters are monitored, such as the overall antioxidant status (quantitative determination of the ability to absorb free radicals) and the damage generated by oxidative stress (lipid peroxidation, protein carbonylation).

Techniques and Planning

Four groups of 10 male rats of the Wistar Hannover strain were operated on, after their reception, in order to put in place a venous catheter. This catheter is introduced via the left jugular and descended to the level of the vena cava, and its proximal part interconnects at the cranial level, where it is secured in place so as to allow blood samples to be taken, in a desired amount, from a conscious animal.

One week later, the rats were divided up into 4 groups subjected to a sucrose-rich diet, containing 14 energy % of proteins, differing according to the nature of the proteins or the amount of cysteine added to the diet:

Diet 0 (C0: control)—P14 total milk proteins.
Diet 1—P14 alphalac (a serum protein concentrate enriched in α-lactalbumin YV9705 prepared by the company ARMOR PROTEINES: providing approximately 4.6 times more cysteine than the control diet).

Diet 2—P14 total milk proteins+cysteine (in the form of N-acetylcysteine) added for a total content equivalent to that of diet 1 (C1).

Diet 3—P14 total milk proteins+cysteine (in the form of N-acetylcysteine) added for a content 13.4 times greater than the control diet (C2).

The compositions of the various foods (C0, alphalac, C1 and C2) are given in the table below in g/kg of food.

| (mg solids in 3 g food) | C0 | alphalac | C1 | C2 |
|---|---|---|---|---|
| Total milk proteins | 420.0 | | 417.6 | 411.8 |
| YV9705 | | 420.0 | | |
| Sucrose | 2168.1 | 2168.1 | 2155.6 | 2125.6 |
| N-acetylcysteine | 0 | 0 | 17.3 | 58.8 |
| Vitamin compound AIN 93 VX | 30.0 | 30.0 | 29.8 | 29.4 |
| Mineral compound AIN 93M | 105.0 | 105.0 | 104.4 | 102.9 |
| Soybean oil | 120.0 | 120.0 | 119.3 | 117.6 |
| Cellulose | 150.0 | 150.0 | 149.1 | 147.1 |
| Choline bitartrate | 6.9 | 6.9 | 6.9 | 6.8 |
| Cysteine content | 3.6 | 16.5 | 16.5 | 48.1 |

Diet No. 2 makes it possible to assess the role of cysteine in comparison with diet No. 1. Diet No. 3 makes it possible to specify the dose-effect within which it lies.

The rats were used to receiving a part of their diet in the form of a calibrated meal to be consumed in a small amount of time.

The blood samples in the postprandial phase are spread out over approximately 3 h, with, over this period: six glycemia assays, three glutathione assays (including reduced and oxidized form) and four insulinemia assays.

After 5 weeks of diet, the rats were sacrificed and the glutathione was assayed in the blood and various organs (liver, muscles, heart). The activity and the expression of γ-glutamyl-cysteine-ligase, a key enzyme in glutathione synthesis, were measured in the liver.

Results:

The postprandial test carried out acutely, after the first ingestion of the experimental meal, confirms the hypothesis of a beneficial effect of a supplementary intake of cysteine on the regulation of glycemia. In fact, the postprandial hyperglycemia and hyperinsulinemia of the animals having consumed the cysteine-rich meals are significantly lower than those of the control animals (FIGS. 2 and 3).

At equal cysteine intake, the effect of the alphalac on glycemia is greater than that of the C1 diet, which suggests that the cysteine incorporated into the α-lactalbumin proteins improves the regulation of glycemia more effectively.

After 4 weeks of diet, the level of oxidative stress in the animals consuming more cysteine, evaluated by the blood and liver glutathione concentrations and the carbonylated proteins in the plasma, was lower than that of the control animals (FIGS. 4 and 5).

Once again, at equal cysteine intake, the effect of the alphalac on oxidative stress is greater than that of the C1 diet, which suggests that the cysteine incorporated into the α-lactalbumin proteins improves the antioxidant status more effectively.

EXAMPLE 3

Study of the Role of Neosynthesized Glutathione in the Improvement of Oral Glucose Tolerance in Response to Cysteine In order to confirm the role of glutathione in the regulation of glycemia and the advantage of α-lactalbumin as a cysteine source from the viewpoint of synthesis of this compound, we used a glutathione-depleted rat model, by inhibiting the synthesis of this compound with buthionine sulfoximine treatment. In these animals, glucose tolerance and insulin sensitivity were measured, and also various parameters related to the oxidative stress state. The replenishing of glutathione stores and the change in the regulation of glycemia were measured in response to diets with various levels of enrichment in α-lactalbumin and cysteine supplementation.

Methodology:

The methodology of example 2, limited to the acute part of the study, was repeated. Four groups of 10 male rats of the Wistar Hannover strain were operated on, after their reception, in order to put in place a venous catheter. This catheter is introduced via the left jugular, descended to the level of the vena cava, and its proximal part interconnects at the cranial level, where it is secured in place so as to allow blood samples to be taken, in the desired amount, from a conscious animal.

One week later, the rats were divided up into 4 groups subjected to the sucrose-rich normal protein meals C0, C1, C2 and alphalac. An injection of buthionine sulfoximine, a glutathione synthase inhibitor, was given beforehand (one hour before the meal). Thus, during the postprandial period, glutathione neosynthesis is inhibited.

Blood samples were taken 15, 45, 75 and 135 minutes after the end of the meal.

Results:

The inhibition of glutathione synthesis cancels out the acute beneficial effect of the cysteine supplementation on postprandial glycemia, thereby suggesting that the effect of the cysteine on the regulation of glycemia involves glutathione synthesis. Conversely, the inhibition of glutathione synthesis does not modify the effect of α-lactalbumin on postprandial glycemia: the beneficial effect of α-lactalbumin on the regulation of glycemia is therefore independent of glutathione synthesis, thereby suggesting that α-lactalbumin has its own effect on the regulation of glycemia (FIG. 6).

EXAMPLE 4

Study of the Long-Term Effect of Cysteine Supplementation on the Insulin Signaling Pathway Methodology:

Four groups of 8 male rats of the Wistar Hannover strain were subjected for 6 weeks to the same sucrose-containing diets as those used in experiments 2 and 3 (P14 containing sucrose, C1, C2 and alphalac). An additional group of 8 rats, this being a non-sucrose control group, fed with a diet P14 containing 14 energy % of total milk proteins without sucrose, was added. This group constitutes the "normal" or "healthy" positive control in the evaluation of the insulin signaling pathway modifications related to the high-sucrose diet.

Before the introduction of the diets and then at 5 weeks, the oral glucose tolerance of the rats is evaluated by means of an oral glucose provocation test. After being made to fast for a minimum of 8 hours, the rats receive a dose of 1 $g.kg^{-1}$ of glucose. Blood samples taken from the tail at 15, 30, 60 and 120 min after the glucose bolus make it possible to monitor the post-glucose plasma glycemia and insulinemia kinetics (FIGS. 7 and 8).

At 3 weeks, a fasting blood sample was taken in order to monitor the change in metabolic parameters and in blood glutathione (FIG. 9).

At 6 weeks, the anesthetized rats receive a dose of 0.750 $mU.kg^{-1}$ of insulin, directly injected into the vena cava. This injection makes it possible to light up the insulin signaling pathway and to evaluate the differences in activation between the various groups. 5 min after the injection, the muscle and the liver are removed, ground in a lysis buffer and directly immunoprecipitated with an antibody which recognizes the IRS1 (insulin receptor substrate 1) protein. The immunoprecipitated samples are then loaded onto a gel and then blotted onto a membrane (Western blotting technique). The membranes are successively hybridized with an antiphosphotyrosine antibody (tyrosine phosphorylation of the IRS protein is the first step in the insulin signaling pathway) and then an anti-total IRS1 antibody (FIG. 10).

At sacrifice, blood and tissue samples were taken for other biochemical analyses. This technique makes it possible to directly evaluate the insulin sensitivity.

Results:

1. Blood Glutathione at 3 Weeks, Tissue Glutathione at 6 Weeks

As shown in FIG. 9 and the table below, the fasting blood GSH ratio (oxidized glutathione/total glutathione) is significantly lower in the C1, C2 and alphalac rats, compared with the P14 and P14 containing sucrose (P14S) rats, with a more marked effect in the rats fed with alphalac. This difference is explained both by a significant increase in total glutathione in the C1, C2 and alphalac rats and a significant decrease in oxidized glutathione in the C2 and alphalac rats. These results confirm that the C1, C2 and alphalac diets are associated with less oxidative stress.

| GSH ratio as % after 6 weeks of diet | | | |
|---|---|---|---|
| | Liver | Muscle | Heart |
| P14 | $1.3^{ab} \pm 0.5$ | $3.7^a \pm 1.4$ | $9.1^b \pm 1.9$ |
| P14S | $1.7^b \pm 0.5$ | $10.6^b \pm 5.4$ | $12.2^a \pm 3.4$ |
| C1 | $1.0^{ac} \pm 0.6$ | $5.5^a \pm 3.7$ | $9.9^{ab} \pm 4.6$ |
| C2 | $0.7^c \pm 0.2$ | $4.8^a \pm 4.0$ | $8.3^b \pm 2.7$ |
| alphalac | $0.9^a \pm 0.3$ | $3.9^a \pm 1.7$ | $10.2^{ab} \pm 2.7$ |

The means sharing the same suffix are not significantly different.

2. Oral Glucose Tolerance Test at 5 Weeks of Diet

The oral glucose tolerance test carried out at 5 weeks confirms the results of example 2 regarding the regulation of glycemia. The rats supplemented with cysteine and the rats fed with the alphalac diet show better glucose tolerance than the control rats: the hyperglycemia and the hyperinsulinemia brought about by the oral glucose load are less substantial in the C1, C2 and alphalac groups than in the P14S group.

Once again, the effect of the alphalac is greater than that of the C1 diet, at an equivalent cysteine dose: α-lactalbumin is more effective than pure cysteine.

The additional information provided by this study compared with study 2 is the comparison with the non-sucrose P14 control. Both with respect to glycemia and to insulinemia, the C2 and alphalac groups are not different from the non-sucrose P14 control (FIGS. 7 and 8, the table below). These results suggest that the C2 dose of cysteine and the α-lactalbumin cancel out the deleterious effect of the sucrose on the regulation of glycemia.

| TOTG: Area under the curve at 5 weeks | | |
|---|---|---|
| | Glucose | Insulin |
| P14 | $2848.1^a \pm 953.9$ | $0.25^a \pm 0.11$ |
| P14S | $3875.6^b \pm 929.8$ | $0.42^b \pm 0.08$ |
| C1 | $3583.1^b \pm 980.2$ | $0.37^b \pm 0.15$ |
| C2 | $2411.2^a \pm 1044.8$ | $0.25^a \pm 0.14$ |
| alphalac | $2351.2^a \pm 585.1$ | $0.35^a \pm 0.20$ |

The means sharing the same suffix are not significantly different.

3. Activation of the Insulin Signaling Pathway

The results obtained in the glucose tolerance tests were confirmed and specified by analyzing the activation of the insulin signaling pathway.

In the muscle, the percentage of tyrosine-phosphorylated IRS1 protein was much lower in the P14S rats than in the non-sucrose P14 rats (FIG. 10). Our results also suggest differences in expression of the IRS protein from one group to the other: in the P14S rats, it seems to be greatly decreased, and this decrease seems to be attenuated by the cysteine supplementation, with a dose effect, and by the α-lactalbumin, which once again has an effect equivalent to the high dose of cysteine.

Conversely, in the liver, no difference was measured, either in percentage of phosphorylated IRS protein or in expression of the IRS protein.

These results demonstrate the molecular action of α-lactalbumin and of cysteine on the insulin signaling pathway and suggest that the action of cysteine and of α-lactalbumin in the prevention of glucose intolerance and insulin resistance occurs mainly at the peripheral level.

The invention claimed is:

1. A method for improving glucose tolerance and/or promoting the cellular absorption of glucose and/or promoting the regulation of glycemia and/or treating the appearance of insulin resistance and/or treating the appearance of the symptoms of type II diabetes and/or treating the appearance of type II diabetes, said method comprising administering to a subject a composition comprising α-lactalbumin or an α-lactalbumin hydrolysate wherein the daily dose of α-lactalbumin is between 30 and 50 grams.

2. The method as claimed in claim 1, wherein the α-lactalbumin originates from human milk, cow's milk, goat's milk, ewe's milk, mare's milk or buffalo milk.

3. The method as claimed in claim 1, wherein the daily dose of α-lactalbumin represents between 10% and 80% by weight of the total daily protein consumption of the subject.

4. The method as claimed in claim 3, wherein the daily dose represents between 20% to 70%.

5. The method as claimed in claim 1, wherein said administering step comprises administering the composition to humans.

6. The method as claimed in claim 1, wherein said administering step comprises administering the composition at mealtimes, within a period ranging from one hour before the meal to a quarter of an hour after the meal.

* * * * *

UNITED STATES PATENT AND TRADEMARK OFFICE
CERTIFICATE OF CORRECTION

PATENT NO. : 8,648,039 B2
APPLICATION NO. : 12/298417
DATED : February 11, 2014
INVENTOR(S) : Tome et al.

It is certified that error appears in the above-identified patent and that said Letters Patent is hereby corrected as shown below:

On the Title Page:

Item (73) Assignee: "Compagnie Laitiere Europeene" should read --Compagnie Laitiere Europeenne--.

On the Title Page:

The first or sole Notice should read --

Subject to any disclaimer, the term of this patent is extended or adjusted under 35 U.S.C. 154(b) by 1015 days.

Signed and Sealed this
Twenty-fourth Day of February, 2015

Michelle K. Lee
*Deputy Director of the United States Patent and Trademark Office*